United States Patent [19]

Tardieu et al.

[11] Patent Number: 4,486,176
[45] Date of Patent: Dec. 4, 1984

[54] HAND HELD DEVICE WITH BUILT-IN MOTOR

[75] Inventors: Pierre R. Tardieu, Chateauneuf-sur-Sarthe; Yves H. Mulet-Marquis, Le Lion d'Angers, both of France

[73] Assignee: Kollmorgen Technologies Corporation, Dallas, Tex.

[21] Appl. No.: 433,527

[22] Filed: Oct. 8, 1982

[30] Foreign Application Priority Data

Oct. 8, 1981 [FR] France ............................ 81 18981

[51] Int. Cl.³ ............................................ A61C 1/12
[52] U.S. Cl. ................................. 433/133; 310/47; 310/103; 310/156; 74/416; 74/DIG. 4; 335/306
[58] Field of Search ................ 310/47, 50, 85, 103, 310/105, 106, 107, 108, 109, 110, 75 R, 104, 156, 86, 89, 92, 95, 97, 114, 168, 169, 170, 88; 335/306; 74/416, DIG. 4; 433/103, 131, 133

[56] References Cited

U.S. PATENT DOCUMENTS

| | | | |
|---|---|---|---|
| 2,768,316 | 10/1956 | Neiss | 310/103 |
| 3,790,889 | 2/1974 | Mincuzzi | 310/103 |
| 3,796,898 | 3/1974 | Kleinwaechter | 310/103 |
| 4,167,848 | 9/1979 | Kitai | 310/114 |
| 4,277,707 | 7/1981 | Silver | 310/104 |
| 4,302,693 | 11/1981 | Burgmeier | 310/156 |

FOREIGN PATENT DOCUMENTS 1441989 7/1976 United Kingdom ............... 433/131

Primary Examiner—R. Skudy
Attorney, Agent, or Firm—Morgan, Finnegan, Pine, Foley & Lee

[57] ABSTRACT

A hand held device with built-in motor for rotational drive of small tools. The hand held device includes an outer housing consisting of a larger diameter rear part which contains an electric driving motor, an intermediate part of small diameter which contains motion transmitting means, and a front part in which is mounted a holder for the tool to be driven. The electric driving motor is a brushless motor having a rotor encapsulated in a sealed insulating enclosure and includes permanent magnets covered with a layer of conducting metal and a stator made up of multi-phase winding coils embedded in a molded plastic material. The motion transmission means consists of non-contacting magnetic coupling means.

7 Claims, 3 Drawing Figures

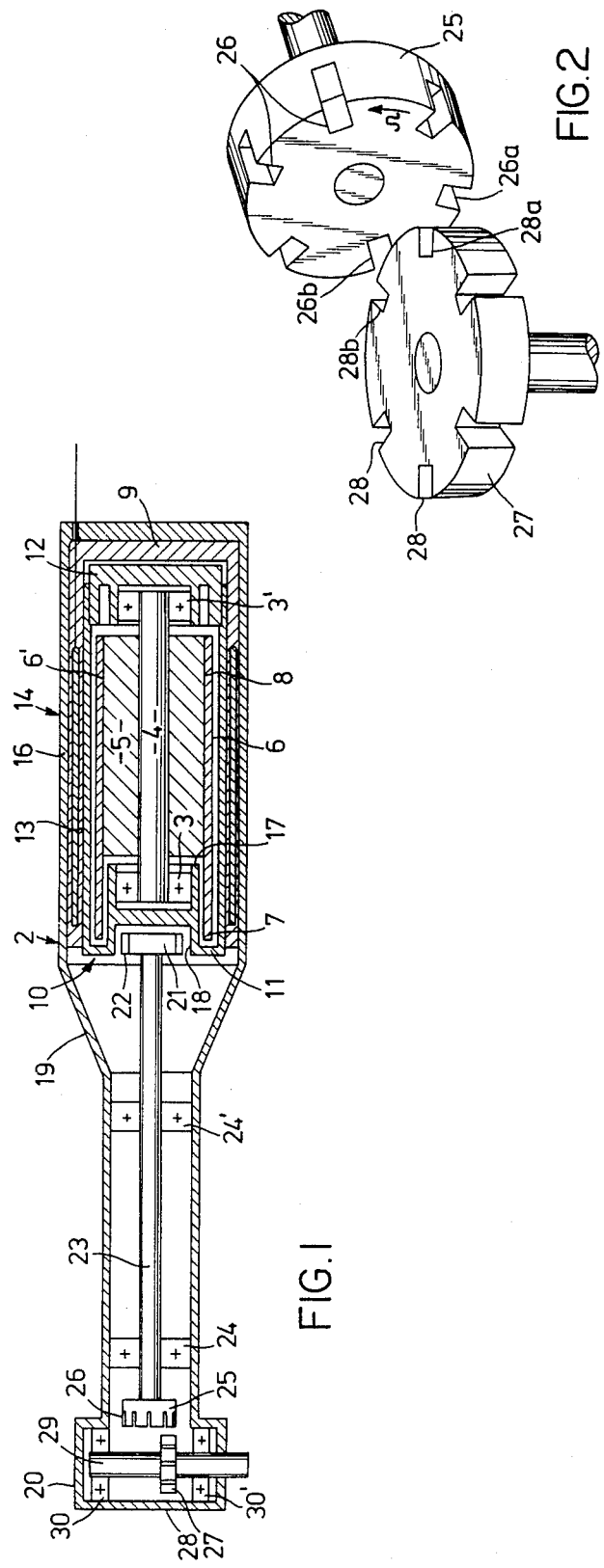
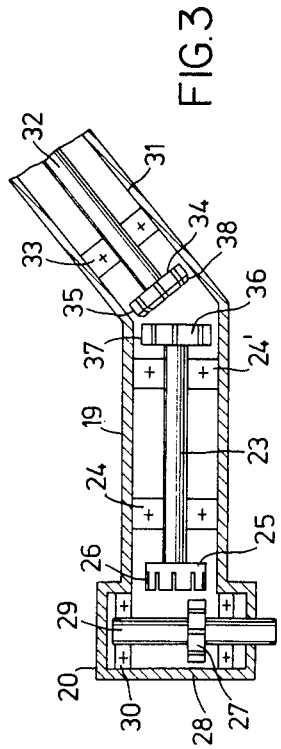

HAND HELD DEVICE WITH BUILT-IN MOTOR

The present invention relates to a hand held piece with integrated motor for driving tools of small dimensions comprising an outer housing with a rear end part of a diameter sufficient for incorporating an electric tool drive motor, an intermediary housing having a conical drive part, and a housing of reduced diameter which carries means for transferring the rotation of the tool drive motor to the tool head.

Hand pieces of the kind described are mainly used in dental surgery. For the drive of the rotating tools several devices such as electric motors and air turbines are known. Air turbines permit high rotating speeds, such as 100,000 rpm and more. The torque of the air turbines at such speeds is, however, rather weak. Besides, such air turbines are very noisy which is a burden for the patient and the practitioner.

Electric motors render a considerable torque at low speeds, about up to 40,000 rpm. Therefore, when using such electric motors in such drives, the electric motor must necessarily comprise a gear train for multiplying the motor rotation speed for high speed tool drive. Such gear trains are very easily damaged by overload. Daily lubrication of the bearings is required. Hand pieces of conventional design are provided with electric motors with brushes. Such brushes are subject to wear and have to be exchanged frequently. The brushes are arranged in the interior part of the motor and their replacement requires a high degree of skill. Furthermore, the motor has to be waterproof for lubricating and water cooling of the tool. Such water causes well-known problems with electricity. Hermetical sealing of such motors is especially difficult in the area of the brushes.

In the present invention, many of the difficulties heretofore encountered are avoided. Rotation speeds as high as conventionally known for air turbines are attained and are combined with the high torque of electric motors. Reliable electric insulation is provided and the safety of the operating tool is substantially increased. Overload is absolutely excluded thus making an automatic device to prevent overload superfluous.

In accordance with the present invention, all these advantages are achieved with a hand piece with integrated toolholder and electric drive motor assembly comprising an outer housing with a rear end part of a diameter sufficient for incorporating the said electric drive assembly, an intermediary part having a conical section, and a head part having a reduced diameter and forming the housing for the toolholder with toolholder shaft. The drive motor is a brushless electric motor which includes a rotor assembly comprising permanent magnets having their co-axial outer surfaces coated with a layer of electrically conductive metal. The rotor assembly is rotatably mounted and hermetically sealed in a rotor housing made of insulating material. The motor assembly further includes a stator assembly having winding coils of a multi-phase field winding embedded in a layer of insulating material. The rotor assembly, as well as one or more transmission shafts and the toolholder shaft, is provided with magnetic coupling means for transmitting the torque generated by the electric motor assembly to the toolholder without mechanical contact of the parts.

The speed of the rotor depends upon the rotational speed of the stator field which, in turn, depends on the frequency of the supply current. The frequency of the supply current is adjustable with conventional means.

Although the electric motor in the hand held piece of the present invention is of small dimension, it permits high speeds comparable to those heretofore achieved with air turbines. For example, with a supply current of 2.000 cycles, a bi-polar motor reaches the speed of 120,000 rpm. The use of magnetic coupling means without mechanical contact avoids mechanical wear and, at the same time, eliminates lubrication problems.

The magnetic coupling means in the instant invention for transmitting the torque from the rotor shaft to the toolholder shaft comprises at least one shaft rotatably mounted in bearings in the center part of the housing, the shaft is provided on both ends with at least one pair of permanent magnets of small dimensions.

In one embodiment of the present invention, the toolholder is rotatably mounted by means of bearings in the head part of the housing. The toolholder shaft is provided with a first disc of plastic material for transmitting the torque generated by the electric motor. The first disc has small permanent magnets arranged regularly about its periphery and embedded in the plastic material.

The magnetic coupling means includes at least one shaft rotatably mounted in bearings in the center part of the housing. The coupling shaft is provided at the end facing the toolholder with a second disc of plastic material having small permanent magnets regularly arranged about its periphery and embedded in said plastic material. The first and second discs form a magnetic coupling. The magnetic coupling insures protection against overload. If the shaft of the toolholder is blocked or jammed, the outer shaft is still freely rotatable without being damaged.

The toolholder shaft and the shaft transmitting the rotation movement may be arranged under an angle of 90° C. to each other or in parallel or in any angle between 0° and 90°. In the latter case, it is advantageous to provide either the first and/or the second disc with a conic part on the side facing the other disc.

In a special embodiment of the invention with an angled housing the transmission shaft cooperating with the hand piece also cooperates with a second transmission shaft and is provided at its second end cooperating with said second transmission shaft with a third disc of plastic material which is also provided with small permanent magnets arranged regularly about its periphery and embedded in said plastic material. The second shaft is provided on its one end with small magnets to receive the rotation movement transmitted by the rotor of the motor. At its other end, the second shaft is provided with a fourth disc made of plastic material and with small permanent magnets arranged regularly about its periphery and embedded in said plastic material, cooperating with the magnets of the third disc thereby providing another magnetic coupling.

Other features and advantages of the present invention will be obvious from the following description taken in connection with the accompanying drawings in which FIG. 1 is a schematic view, in axial section, of one embodiment of the hand piece in accordance with the invention;

FIG. 2 is an enlarged partial view of the magnetic coupling means as used in the hand piece in accordance with the invention; and FIG. 3 is a partial view of an axial section of another embodiment in accordance with the invention and includes an angled housing.

The hand piece of FIG. 1 comprises an outer housing generally designated 2, with a rear end part 16 of a diameter sufficient for incoporating the electric motor assembly generally designated 14. Housing 2 includes an intermediary part 19, having a conical section, and a head part 20 with reduced diameter connected to intermediary part 19. The rear part 16 consists of metallic material housing small brushless electric motor 14 of the type disclosed in copending patent application Ser. No. 433,526 Brushless Electric Micromotor filed concurrently herewith.

Electric motor 14 comprises a rotor assembly hermetically sealed in plastic housing 10 with capsule 11 at one end and flange part 12 at its other end. A stator assembly comprising winding coils of a multi-phase field winding 13 embedded in a layer of insulating material 9 inside of housing 16. The field winding of stator 13 may consist of three winding coils. The angular distance between the coils of the field winding is $2\pi/3$ and are connected to a tri-phase electric power supply providing a phase difference between the phases of $2\pi/3$.

The rotor comprises a shaft 4 rotatably mounted in bearings 3 and 3' inside of the plastic housing 10, a tube-like part 5 made of magnetic material fixed to shaft 4 and carrying permanent magnets 6 and 6' with opposite poles having coaxial surfaces coated with a layer of electrically conductive metal 8. Plastic rotor housing 10 is recessed at its front with a recessed part 17, forming an axial cylindric cavity 18 facing to the outside. Portions 7 of the permanent magnets 6 and 6' extend into the sleeve formed inside of said housing 10 by the recessed part 17 thus providing one part of a magnetic coupling for transmitting the rotor torque to an outside shaft 23. Shaft 23 is provided at the motor end with a magnetic coupling plastic disc 21 having two diametrically opposed permanent magnets 22 embedded in the periphery of disc 21. Shaft 23 is supported by bearings 24 and 24' in known manner which are arranged inside the center part 19. At the other end of shaft 23 there is mounted a disc 25 of plastic material provided on its front face with small permanent magnets 26, FIGS. 1 and 2, regularly arranged about the periphery of the front faces and embedded in the plastic material. The head part 20 of the toolholder comprises tollholder shaft 29 rotatably mounted in bearings 30 and 30'. Shaft 29 is provided with a disc 27 made of plastic material having small permanent magnets 28 regularly arranged about its periphery and embedded in the plastic material. Disc 27 is magnetically coupled through permanent magnets 26 and 28 with disc 25 and transmits the torque from shaft 23 to shaft 29.

For explanatory purposes it is assumed that discs 25, 27 have adjacent magnets 26a and 26b and 28a and 28b, respectively. Disc 25 rotates counterclockwise so that magnet 26a will react with magnet 28a of disc 27 and disc 27 will start rotating clockwise until magnet 26b will get close to magnet 28b, etc. If both discs 25 and 27 have the same diameter and the same number of embedded magnets, they will rotate with the same speed. If so desired, different numbers of magnets may be on the adjacent disc thereby achieving a change in speed of rotation. It is only required that the magnets are arranged on the respective disc in equal distances from each other about the periphery of the disc. In operation, the portions 7 of the permanent magnets 6.6' extending into the sleeve formed inside of the housing 10 rotating when the motor is energized and providing magnetic coupling with the magnets 22 of the disc 20 of transmission shaft 23, causing transmission shaft 23 to rotate with the shaft 4 of the rotor. As the transmission shaft 23 rotates, plastic disc 25 at the transmission shaft 23 rotates, providing magnetic coupling with the permanent magnets 28 in plastic disc 27 of shaft 29. Thus, when the motor is energized, shafts 23 and 29 are rotated through the magnetic couplings caused by the permanent magnets mounted in the plastic discs on the respective shafts.

In FIGS. 1 and 2 the shafts of discs 25 and 27 are arranged at an angle of 90° to each other, the magnets 26 being on the front surface of disc 25 and cooperating with magnets 28 arranged about the periphery of disc 27, thus providing for a minimum distance between the magnet surfaces. The same concept of magnetic coupling can be used with discs having their shafts arranged in parallel or under any desired angle. The arrangement of the embedded magnets should be such that the distance of the surfaces of the magnets on both discs is a minimum, without touching, so that the magnets can cooperate with each other. To make sure that the distance between the magnet surfaces is a minimum, it is suggested that, when the shafts are arranged under an angle of other than 90°, one of the discs is provided with a conical part for embedding the magnets. It is a special advantage of the magnetic coupling means of the present invention that, in case disc 27 should be jammed, disc 25 is freely rotatable without any damage to the discs, shafts, magnets or motor. The magnetic coupling described makes mechanical protection system unnecessary.

FIG. 3 shows an embodiment of the invention having an angled housing. In this embodiment, the head part 20 with toolholder 29 is identical with the embodiment shown in FIG. 1. Mounted on toolholder shaft 29 is the disc 27 provided with the small permanent magnets 28 cooperating with the small magnets 26 of disc 25 mounted on the front end of transmission shaft 23. The rear end 16 of the housing accommodating the motor, not shown in FIG. 3, is identical with the respective part shown in FIG. 1.

The hand piece shown in FIG. 3 is angled and has an additional shaft 32 for transmitting the torque from the shaft 4 of electric motor 14 (FIG. 1) to shaft 23 which drives toolholder shaft 29. Additional shaft 32 is mounted in bearings 33 and 33' arranged in intermediary part 31 of the housing. Shaft 32 has mounted on its rear end (not shown in FIG. 3) the equivalent of part 21 with magnets 22 of FIG. 1.

Additional shaft 32, FIG. 3, is provided at its front end with a plastic disc 34 similar to discs 25 and 27 with a number of small magnets 35 regularly spaced and embedded in its periphery. Disc 34 cooperates with another disc 36 similar to discs 25, 27 and 34 and mounted on the rear end of shaft 23. Discs 34 and 36 are arranged under an angle towards one another. Preferably, one of the discs, e.g., disc 34, has a conical edge 38, thus providing for parallel surfaces of magnets on both discs at the locus of minimum distance between the discs.

The hand pieces in accordance with the present invention may comprise several angled parts and, in such case, having more than two transmission shafts 23 and 32 under an angle toward one another and interacting magnetically. The coupling system between two shafts in series is the same as hereinabove described using discs provided with a number of permanent magnets evenly spaced on their peripheries and embedded in the plastic material of the discs. Thereby, the advantages of the present invention are realized, which comprise the automatic protection from mechanical overload, the almost complete avoidance of wear of the transmission means, the possibility of a lifetime lubrication of the bearings and the simple mode of exchanging the rotor.

The terms and expressions which have been employed are used as terms of description and not of limitation, and there is no intention, in the use of such terms and expressions, of excluding any equivalents of the features shown and described or portions thereof, but it is recognized that various modifications are possible within the scope of the invention claimed.

What is claimed:

1. A hand held piece with integrated toolholder and electric drive motor assembly comprising, an outer housing with a rear end part of a diameter sufficient for incorporating an electric drive motor assembly, an intermediary housing having a conical section, and a tool head housing having a reduced diameter and forming a housing for the toolholder, a toolholder shaft in said toolholder housing, at least one pair of permanent magnets mounted in a plastic disc at the end of said toolholder shaft a brushless electric motor drive assembly having a rotor assembly comprising permanent magnets having coaxial outer surfaces coated with a layer of electrically conductive metal mounted on a rotor shaft, one end of said rotor assembly permanent magnets extending beyond the end of said rotor shaft, said rotor shaft being rotatably mounted and hermetically sealed in said outer housing on a rotor housing of insulating material, said motor assembly further having a stator assembly having winding coils of a multi-phase field winding embedded in a layer of insulating material and at least one transmission shaft between said rotor shaft and said toolholder shaft, said transmission shaft having, at each of its ends, a plastic disc, each of said transmission shaft discs having at least one pair of permanent magnets, said one end of said rotor assembly permanent magnets extending beyond the end of said rotor shaft and said permanent magnets in said plastic disc and at one of the ends of said transmission shaft forming a magnetic coupling when said electric motor rotor is rotated to rotate said transmission shaft, the permanent magnets in the plastic disc at the other end of said transmission shaft forming magnetic coupling with the permanent magnets in the plastic disc on said toolholder shaft.

2. A hand held piece, as recited in claim 1, wherein said toolholder shaft is mounted in bearings and wherein said toolholder shaft is provided with a disc made of plastic material, said toolholder shaft disc being provided with small permanent magnets which are regularly arranged about the periphery of said disc and embedded in the plastic material.

3. A hand held piece, as recited in claim 2, wherein said transmission shaft disc at toolholder shaft end of said toolholder shaft and said toolholder shaft disc are arranged at an angle of 90° to each other and are located to form a magnetic coupling for transmitting torque from said shaft to said toolholder.

4. A hand held piece, as recited in claim 2, said transmission shaft disc and said toolholder shaft disc, as well as the respective shafts, are arranged parallel to each other.

5. A hand held piece, as recited in claim 2, wherein said transmission shaft is provided with a disc and said transmission shaft disc and said toolholder shaft disc are arranged at an angle to each other.

6. The hand piece of claim 5 wherein one of said discs is provided with a conical portion for providing parallel surfaces of magnets on said discs at the locus of minimum distance between said discs.

7. A hand held piece, as recited in claims 1, 2, 3, 4, 5 or 6, said permanent magnets in said plastic discs on said toolholder shaft and said transmission shaft are regularly arranged about the periphery of said plastic discs and embedded in said plastic material.

* * * * *